(12) United States Patent
Schneider et al.

(10) Patent No.: US 12,185,927 B2
(45) Date of Patent: Jan. 7, 2025

(54) INPUT UNIT FOR A MEDICAL INSTRUMENT AND MEDICAL SYSTEM WITH AN INPUT UNIT

(71) Applicant: KARL STORZ SE & Co. KG, Tuttlingen (DE)

(72) Inventors: Janosz Schneider, Tuttlingen (DE); Dominik Längle, Tuttlingen (DE); Sven Axel Grüner, Tuttlingen (DE); Jochen Stefan, Tuttlingen (DE); Thorsten Ahrens, Tuttlingen (DE)

(73) Assignee: KARL STORZ SE & Co. KG, Tuttlingen (DE)

( * ) Notice: Subject to any disclaimer, the term of this patent is extended or adjusted under 35 U.S.C. 154(b) by 368 days.

(21) Appl. No.: 17/869,878

(22) Filed: Jul. 21, 2022

(65) Prior Publication Data

US 2023/0029607 A1 Feb. 2, 2023

(30) Foreign Application Priority Data

Jul. 28, 2021 (DE) ...................... 10 2021 119 641.8

(51) Int. Cl.
*A61B 17/00* (2006.01)
(52) U.S. Cl.
CPC .................... *A61B 17/00234* (2013.01); *A61B 2017/00367* (2013.01)
(58) Field of Classification Search
USPC ........................................................ 700/83
See application file for complete search history.

(56) References Cited

U.S. PATENT DOCUMENTS

| 5,454,827 A | 10/1995 | Aust et al. |
| 7,113,836 B2 | 9/2006 | Hörnig |

(Continued)

FOREIGN PATENT DOCUMENTS

| DE | 102004010205 B3 | 10/2005 |
| DE | 102017103199 A1 | 8/2018 |

(Continued)

OTHER PUBLICATIONS

German Office Action for corresponding German Patent Application No. 10 2021 119 641.8, mailed May 3, 2022.

*Primary Examiner* — Mohammad Ali
*Assistant Examiner* — Joshua T Sanders
(74) *Attorney, Agent, or Firm* — Jason H. Vick; Womble Bond Dickinson (US) LLP (57) ABSTRACT

An exemplary embodiment relates to an input unit (10) for operating a medical instrument (12) with a hollow shaft (14) extending along a longitudinal axis (L) for receiving guide wires (20), with a tool (16) arranged on the distal side of the shaft (14), extending along an extension axis (E) and a control unit (18) arranged proximally on the shaft (14) for handling the tool (16) by means of the guide wires (20), comprising first input means (22) for continuous, pivoting and rotation-true, preferably uninterrupted and/or absolute, conversion of an ergonomically limited user input, in particular a natural user movement of movable first operating means, into an adjustment movement of the tool (16) in a first handling mode, in order to pivot the tool (16) by means of the control unit (18) relative to the longitudinal axis (L) in a limited way and/or to rotate about the extension axis (E) in a limited way.

19 Claims, 5 Drawing Sheets

(56) References Cited

U.S. PATENT DOCUMENTS

| | | | | |
|---|---|---|---|---|
| 2005/0195946 A1* | 9/2005 | Hornig | ............... | A61B 6/467 |
| | | | | 378/204 |
| 2018/0228560 A1* | 8/2018 | Ziegenspeck | ......... | A61B 34/70 |
| 2021/0038331 A1* | 2/2021 | Grüner | ............... | A61B 17/29 |
| 2021/0379332 A1* | 12/2021 | Komp | ................. | A61B 34/20 |

FOREIGN PATENT DOCUMENTS

| | | |
|---|---|---|
| DE | 102017123163 A1 | 4/2019 |
| DE | 102019121092 A1 | 2/2021 |
| EP | 3919021 A1 | 12/2021 |

\* cited by examiner

INPUT UNIT FOR A MEDICAL INSTRUMENT AND MEDICAL SYSTEM WITH AN INPUT UNIT

CROSS-REFERENCE TO RELATED APPLICATIONS

This application claims the benefit under 35 U.S.C. 119(a) to German Patent Application No. 10 2021 119 641.8, filed 28 Jul. 2021, the disclosure of which is incorporated herein by reference in its entirety.

BACKGROUND

One exemplary embodiment relates to an input unit for operating a medical instrument according to the preamble of claim 1. Furthermore, one aspect of the disclosed technology relates to a medical system with at least one input unit and at least one medical instrument.

A generic input unit for operating a medical instrument is known from U.S. Pat. No. 5,454,827 A, for example.

The known medical instrument comprises a hollow shaft extending along a longitudinal axis for receiving guide wires, the shaft having a tool formed along an extension axis on the distal side and a control unit on the proximal side, which is formed for handling the tool using the guide wires. The control unit has a spatially adjustable disc which is coupled to four guide wires and can pivot the tool relative to the longitudinal axis via pivoting members arranged on the distal side.

To control the handling of the medical instrument, a generic input unit with first input means is provided, which can be operated by an operator's hand. Ergonomic user inputs from the operator are thus converted continuously, that is to say pivoting and/or rotation-true, to the handling of the tool. In addition to simply pivoting the tool to influence the orientation, the tool can also be handled via operating means, in particular using operating means interacting with the index finger of the operator, for example to adjust a tool designed as a jaw part between an open and closed state. Furthermore, a limited rotation of the tool can be implemented by rotating the gripped input unit, wherein the rotation is represented by the natural freedom of movement of the operator's hand and/or arm.

When controlling the medical instrument, the adjustment movements of the tool always follow the natural movements of the operator's hand or arm, specifically in an uninterrupted and/or absolute manner. In other words, the mechanically coupled tool continuously follows the operator's ergonomically limited user inputs so that the operator is always in control of the tool and precise work is thus made possible during operational use.

As a result, the generic input units enable minimally invasive medical operations to be carried out precisely, for example in order to take tissue samples, sew up tissue or carry out other operational actions in a sensitive environment.

A disadvantage of the known input unit is the limited and/or restricted handling of the tool, since the natural user movement is reproduced pivoting and/or rotation-true, which is why, in addition to the mechanical and/or structural limitation of the tool, there is a limitation due to the degree of natural freedom of the operator's movement.

Furthermore, medical instruments are also known, which, by means of a spindle, enable the tool to rotate in a mechanically limited manner in some areas for a limited range of rotation. Input units are used for the control, which enable the tool to be controlled in a rotation-true manner, wherein the operator breaks the restricted freedom of movement in the control system to overcome the operator's restricted freedom of movement, such that the operator grasps the first input means, or there is a brief interruption and/or decoupling between the input unit and the tool for resetting and/or returning the first input means, which is always associated with a momentary loss of control over the tool.

Moreover, now a promising further development of the medical instrument is described, which is described in document DE 10 2019 121 092 A1 of the applicant. To put it simply, improved mechanics now make it possible for the tool to rotate endlessly about its extension axis. Advantageously, the rotation of the tool can also be carried out independently of the pivoting of the tool, which is why the field of application of the medical instrument is significantly expanded. The control of a medical instrument that has been further developed in this way is now problematic, since the control of an endless rotation can no longer be reproduced in a pivoting and/or rotation-true manner of the user movement. Since in operational use two tools are usually controlled using each hand of the operator, control using two-hand operation is ruled out. Furthermore, the operator should always retain control of the tool, so that there is always an uninterrupted coupling between the first input means and the tool, regardless of the control of the endless rotational movement of the tool, in order to ensure that the user movements are reproduced in a pivoting and/or rotation-true on the tool.

One exemplary aspect is therefore based on the object of proposing an input unit which overcomes the disadvantages known from the prior art. In particular, the one aspect is to specify an input unit which, despite the continuous, pivoting and/or rotation-true conversion of an ergonomically limited user input, makes it possible to control an endless rotation of the tool.

Furthermore, the object consists of specifying a medical system with at least one input unit and at least one medical instrument.

This object is achieved by an input unit having the features of claim 1. Furthermore, the object is achieved by a medical system according to the present disclosure.

Advantageous developments of the disclosed technology are specified in the dependent claims. All combinations of at least two features disclosed in the description, the claims and/or the figures fall within the scope of the present disclosure.

An input unit with first input means and second input means is provided within the scope of the present disclosure. The input unit according to one aspect of the present disclosure is designed for operating a medical instrument with a hollow shaft extending along a longitudinal axis for receiving guide wires, with a tool being arranged at a first or distal end of the shaft, which extends along an extension axis. Furthermore, a control unit for handling the tool by means of the guide wires is provided at a second or proximal end of the shaft. The first input means are designed for the continuous, pivoting and/or rotation-true conversion of an ergonomically limited user input from an operator into an adjustment movement of the tool in a first handling mode, in order to pivot the tool relative to the longitudinal axis using the first input means using the guide wires via the control unit and/or to rotate about the extension axis. Due to the structural design of the shaft, which is designed to be rigid in some areas, a pivoting of the tool in relation to the longitudinal extent of the shaft is only possible over a limited pivoting range. Furthermore, the rotation of the tool is only possible over a limited range of rotation, which is due to the natural mobility of the operator, in particular a hand of the operator gripping the first operating means, which then in relation to the continuous, i.e., absolute, introduction of a rotation due to the structure of the human arms and whose ergonomics are limited in terms of the range of rotation.

According to an exemplary embodiment, operating means for handling the tool are provided as the first input means, which continuously, i.e., without an interruption in the coupling between the operating means and the tool, map a translation, embodiment and/or transformation of the ergonomic user input into the handling of the tool.

Furthermore, the input unit according to an exemplary embodiment comprises second input means, which are designed for at least partially and non-absolutely converting, reshaping and/or translating at least one further user input from the operator in order to control an endless rotational movement of the tool about its extension axis in a second handling mode.

Advantageously and according to an exemplary embodiment, the first input means enable the reproduction of an ergonomic user input by the operator into a precise and continuous control and/or handling of the tool, whereby, despite the precise and continuous control of the tool by means of the first input means, the endless rotation of the tool can also be controlled by the second input means through the further user input.

For the technical embodiment of the first input means, the scope of the present disclosure provides that they are designed as operating means that can be moved to a limited extent in a first actuating section, in particular a control handle or joystick or a cardan suspended operating means with a gimbal, in particular a tweezer handle. The first actuating section is preferably delimited by a switching means, in particular in the form of a mechanical stop or a type of pressure point. The operating means are designed in such a way that movements can be detected in all degrees of freedom and can be gripped by one of the operator's hands, with at least one of the degrees of freedom preferably being limited by the switching means in the first actuating section. A change in the position of the operating means in relation to a basic position can advantageously be detected and converted into a corresponding positioning of the tool. In this context, it is again pointed out that the rotation of the tool preferably cannot be limited or not only by the operating means in the first actuating section, but it is additionally limited by the freedom of movement of the operator's hand and/or arm, since there should be no change of grip or a brief interruption of the control by means of the first input means.

In this context, it is further pointed out that the tool is preferably used as a jaw part, in particular a jaw clamp, forceps, intestinal forceps, scissors, a needle holder, a probe hook or the like, formed as a surgical tool.

Within the scope of the present disclosure, the second input means are designed as switching means for switching the user input of the operating means between the first and the second handling mode, wherein the switching means can be switched over when an application of force and/or torque to the operating means reaches and/or exceeds a threshold value. In the switched state, the operating means are therefore intended to control the endless rotational movement of the tool about its extension axis in the second handling mode.

In other words, the input unit according an exemplary embodiment enables the first input means to map an ergonomic user input of an operator into the handling of the tool in the first handling mode, which is pivoting and/or rotation-true. The operator thus advantageously retains full control over the tool at all times via the first operating means. On the other hand, the input unit according to an exemplary embodiment includes the second input means, which enable the endless rotation of the tool to be controlled in the second handling mode. It should be noted here that the ergonomic user input in the first handling mode and the first actuating section is preferably not influenced by the switching means. The operating means can only be switched over to the second handling mode when the threshold value of the application of force and/or torque, a kind of pressure point, is reached and/or exceeded.

By moving or rotating the operating means around an initial position, the position and orientation of the tool can be changed through ergonomic user input. The ergonomic user movement can be mapped to the tool via the control unit and the guide wires in a pivoting and/or rotation-true way.

Furthermore, the second input means comprise the switching means already mentioned, which can be switched over to the operating means depending on the force and/or torque applied to the operator. The second handling mode can be activated by switching over the switching means, and the user input is therefore not absolutely converted into an endless rotation of the tool.

Advantageously, the switching means according to an exemplary embodiment can be combined or retrofitted with a large number of operating means for controlling the medical instrument, with the switching means being controllable by means of the ergonomic user input itself by applying force and/or torque, and with the operating means interacting with the switching means in particular outside of the first actuating section. As a result, the operator can, preferably with one hand, enter the ergonomic user input via the operating means and actuate the switching means for activating the second handling mode at the same time, in particular without having to change his or her grip. Therefore, the switching means according to an exemplary embodiment allows uninterrupted control over the movement of the tool in both handling modes and in the transition from the first to the second handling mode.

In a preferred embodiment, the operating means are designed as a control handle, in particular a joystick, which can be pivoted to the basic position, and in particular a base plate, with a rotary element or rotary wheel, the rotary element being mounted so as to be rotatable about an extension axis of the control handle. User movements, in particular pivoting and/or rotational movements, can be detected by means of the control handle with rotary element, in order to transmit these user movements to the tool in the first handling mode in a true pivoting and/or rotational manner.

In a further preferred embodiment, the operating means are in the form of a tweezer handle, preferably in the form of a cardan suspended pressure element. The pressure element has contact surfaces that can be gripped between the thumb and forefinger of one of the operator's hands, in particular, in order to deform the pressure element from a basic position by means of a force that can be applied by hand, in order to handle the tool and, for example, close a jaw part. Furthermore, the pressure element is coupled to a cardan suspension via a carrier element with a rotation mechanism in order to record all user movements acting on the pressure element, in particular pivoting and/or rotational movements, and to transmit them to the tool in the first handling mode in a true pivoting and/or rotational manner.

It should be noted here that the above-mentioned first adjustment section is preferably an actuating section of rotatable operating means, in particular the rotatable rotary element of the control handle or the rotatable pressure element of the tweezer handle. The ergonomic user input and the switching means can thus preferably be operated simultaneously by rotating the rotatable operating means, with the further user input also being able to be operated with the rotatable operating means by switching over the switching means. The rotatable operating means are rotated when the torque is applied, and when the threshold value is reached and/or exceeded, the switching means can be activated, in particular as a stop that counteracts the rotation, and at the same time further user input can be controlled by means of the rotatable operating means in an endless rotation of the tool.

Alternatively, the switching means can preferably also be in operative contact with the operating means along an extension axis of the rotatable operating means, in particular in the base plate of the control handle or in the cardan suspension of the tweezer handle. As a result, the switching means can be operated preferably with a translational movement or application of force along the extension axis, in particular the extension axis of the control handle or the tweezer handle, when the threshold value is reached and/or exceeded. The switching means are therefore not directly coupled to the rotatable operating means by the rotational movement. Here, too, it is preferably not necessary to change the grip to operate the switching means. In this case, the operating means are not limited by a stop with regard to the control possibilities of the tool. In other words, the degree of freedom that is limited here does not correspond to that which is responsible for the movement of the tool.

In the switched state of the switching means, the operating means can therefore be operated in the second handling mode. When using the control handle as an operating means, the endless rotation of the tool can be controlled with the additional user input, preferably by rotating the rotary element. Furthermore, when using the tweezer grip as the operating means, a rotation mechanism of the pressure element is designed in such a way that it can be rotated about a rotation axis for controlling the further user input, i.e., for controlling the endless rotation movement, in the second handling mode, preferably independently of the cardan suspension. By rotating the rotary element or the tweezer handle, a direction of rotation and preferably also an output angular speed or rotational speed of the endless rotational movement of the tool can be controlled by an input angle.

In a further development, the scope of the present disclosure provides that the switching means with the operating means forms a mechanical stop, in particular a pressure point, for switching between the first and the second handling mode in a second actuating section of the operating means. In this second actuating section, the operating means are in mechanical contact with the switching means. As a result, the ergonomic user input can preferably be carried out independently of the switching means in the first actuating section. It is only possible to switch to the second handling mode by applying an increased force and/or torque to the operating means and reaching and/or exceeding the second actuating section, in particular without changing the grip or actuating an additional switching means.

The operating means preferably comprise first restoring means and the switching means comprise second restoring means, with a restoring force and/or torque of the second restoring means forming the threshold value for switching over the switching means. In particular, the operating means are mounted on the first restoring means and the switching means with the second restoring means, with an ergonomic user input, in particular an application of force and/or torque, being able to be carried out in the first actuating section of the operating means, contrary to the first restoring means, until reaching and/or exceeding the threshold value; the operating means are adjusted in relation to the first restoring means in such a way that the operating means are in mechanical contact with the switching means. The threshold value or the required application of force and/or torque for switching over the switching means can therefore be set with the restoring means. In other words, the switching means is a type of kickdown mechanism, with the second restoring means counteracting the user input as a kind of pressure point with an increased movement resistance and the switching means can only be switched over when this resistance is reached and/or exceeded.

In a preferred embodiment, the first and second restoring means are coupled in a series connection, in particular arranged to act in the same adjustment direction, the first restoring means connecting the operating means to the switching means and the first restoring means being adjustable or deformable in such a way that when reaching and/or exceeding the threshold value of the application of force and/or torque, the mechanical stop is formed. In this series connection, when the threshold value is reached and/or exceeded, preferably only the second resetting means counteract the further user input.

In this context, it is preferably provided that a restoring force and/or torque of the first restoring means is smaller than that of the second restoring means, the restoring force and/or torque preferably being adjustable by selecting a spring stiffness. In the first actuating section, the operating means can therefore be adjusted counter to the first restoring means, with the second restoring means and the switching means being essentially unaffected or preferably not adjusted as a result of the lower spring stiffness. In particular, due to the higher restoring force and/or torque of the second restoring means, an increased resistance and a kind of pressure point can be formed on the user input.

In an alternative embodiment, the first and second restoring means are decoupled from one another and the actuating direction of the operating means and the actuating direction of the switching means are arranged at an angle to one another and the mechanical stop already described is formed by a geometric projection in the operating means when the threshold value is reached and/or exceeded, in particular a projection that is flattened in relation to the actuating direction of the switching means, or a chamfer on one side. In this case, the first and second restoring means are preferably mounted independently of one another in comparison to a series connection.

In this context, provision is preferably made for the switching means to be designed as a preferably linearly bearing ball, in order to roll or slide in mechanical contact with the operating means on its geometric projection, in particular over the chamfer. In the first actuating section, the operating means can still be adjusted counter to the first restoring means. When the threshold value of the application of force and/or torque is reached and/or exceeded, the geometric projection, in particular the flattened projection or chamfer, comes into contact with the ball and thus counteracts the user input as a pressure point or increased resistance. The geometric projection is designed such that further adjustment of the operating means in the second adjustment section and the second handling mode causes the ball to roll or slide along the geometric projection and at the same time be adjustable in the angularly arranged actuating direction of the switching means.

Adjusting the switching means also results in a switchover to the second handling mode, as a result of which a further user input on the operating means is converted into an endless rotational movement of the tool.

The first and/or the second restoring means are particularly and preferably a pressure spring and/or a torsion spring. A pressure spring can preferably be used in the case of a translational or force-loaded actuating movement of the operating means. A torsion spring can preferably be used in the case of a rotary or torque-loaded actuating movement of the operating means.

In a preferred embodiment, the operating means are rotatably mounted, in particular by means of the torsion spring as the first restoring means, with the geometric projection being arranged radially. In particular in the second actuating section, the geometric projection is in mechanical contact with the switching means, the switching means being able to be triggered or switched over by applying a torque to the operating means.

The operating means are preferably a pivotable and/or rotatable joystick or control handle with a rotary element or a tweezer handle with a cardan suspension. As already mentioned, the switching means can be actuated in particular by applying a torque to the rotatable rotary element of the control handle or the rotatable tweezer handle. Alternatively, the switching means can also be actuated by applying a force to the control handle, preferably along the extension axis of the control handle, or to the cardan suspension of the tweezer handle.

In addition, within the scope of the present disclosure, protection is claimed for a medical system, in particular an end effector and/or a surgical robot, which has at least one input unit and at least one medical instrument.

The at least one medical instrument includes a hollow shaft extending along a longitudinal axis, a control unit, and a tool for surgical use.

The shaft is designed to receive guide wires for mechanically steering the tool, the tool being arranged at a distal end of the shaft and extending along an extension axis.

The control unit is arranged on the proximal end of the shaft and is operatively connected to the tool via the guide wires in order to pivot the tool in a first handling mode, in particular to pivot it and to rotate it to an ergonomically limited extent, wherein the tool also can be rotated endlessly via the control unit in a second handling mode.

A preferred medical instrument is described in document DE 10 2019 121 092 A1 of the applicant, wherein full reference is made to the corresponding disclosure and the disclosed features of the medical instrument are hereby incorporated herein by reference in their entirety in the application as part of the disclosure as part of a further development.

The medical instrument preferably has a spatially adjustable disc in order to pivot the guide wires along the longitudinal axis of the shaft, the disc being rotatable about the longitudinal axis together with the shaft and the guide wires, and the control unit preferably being designed to pivot the disc.

The tool is preferably in the form of a jaw part, in particular, a forceps, intestinal forceps, scissors, a needle holder, a probe hook or the like, formed as surgical tool.

BRIEF DESCRIPTION OF THE DRAWINGS

Further advantages and details of the invention result from the following description of preferred embodiments as well as from purely schematic drawings.

Showing.

DETAILED DESCRIPTION

Identical elements or elements with the same function are provided with the same reference numbers in the figures.

Figure 1:
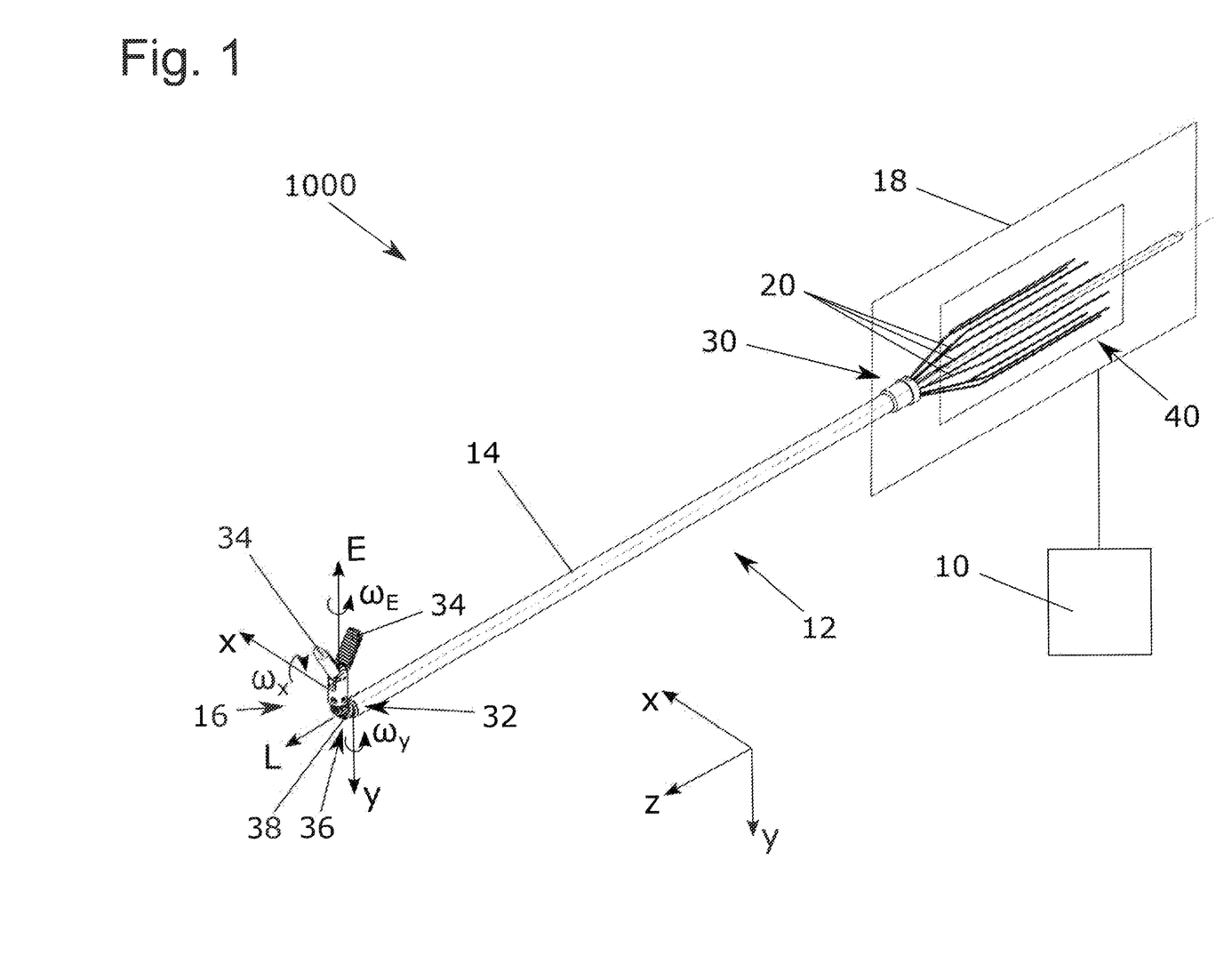
FIG. 1: a perspective view of a medical instrument with an input unit according to an exemplary embodiment shown purely symbolically, in FIG. 2a to FIG. 2c: a perspective view of a tool of the medical instrument according to FIG. 1 and schematized first input means of the input unit according to an exemplary embodiment, in FIG. 3a to FIG. 3c: a perspective view of the known tool from FIG. 2 and schematized second input means of the input unit according to an exemplary embodiment, in FIG. 4a: a cross-sectional view of a first embodiment of the input unit with operating means and switching means in a first actuating section, in FIG. 4b: the input unit according to FIG. 4a in a second actuating section, in FIG. 5a: a second embodiment of the input unit according to FIG. 4a in the first actuating section, in FIG. 5b: the input unit according to FIG. 5a in the second actuating section.

In FIG. 1 a medical system 1000 with a medical instrument 12 is illustrated, which can be operated using a control unit 10 according to an exemplary embodiment designed as a black box. The medical instrument 12 has a hollow shaft 14, which on the proximal side or at a proximal end 30 includes a control unit 18, also illustrated only as a black box, and on the distal side or at a distal end 32, a tool 16, the tool 16 being connected to the control unit 18 in operative connection via guide wires 20.

The control unit 18 enables an endless rotary drive of the tool 16 illustrated in the figure, which is pivoted by 90°. A control unit 18 can be used for this purpose, for example, as is known from the aforementioned document DE 10 2019 121 092 A1 of the applicant.

The tool 16 is a tool 16 provided with two jaw elements 34, in particular a jaw part 17, the two jaw elements 34 also being adjustable between an open state and a closed state via the control unit 18 like a forceps.

The tool 16 can be pivoted via a joint mechanism 36 relative to the longitudinal axis L of the shaft 14, wherein the joint mechanism 36 is formed by pivoting members 38 arranged at the distal end 32 of the shaft 14, which are connected via guide wires 20 running in the longitudinal direction L of the shaft 14 with an unillustrated drive 40 in the figure and arranged at the proximal end 30 of the shaft 14, such that a movement of the drive 40 on the proximal side and a corresponding relative movement of the pivoting members 38 on the distal side causes the tool 16 to pivot.

A corresponding drive 40 is known, for example, from the aforementioned document DE 10 2019 121 092 A1 of the applicant. The guide wires 20 are connected on the proximal side to a disc, not illustrated in the figure, which can be spatially pivoted and rotated by means of the drives 40. The pivoting of the disc causes the guide wires 20 to partially stretch along the longitudinal axis L of the shaft 14 and the tool 16, which extends in a z-direction of a Cartesian coordinate system, can pivot proportionately about the spatial axes x, y of the Cartesian coordinate system by means of the joint mechanism 36. The pivoting movements $\omega_x$, $\omega_y$ around the spatial axes x, y thus enable a spatial orientation of the tool 16.

Due to the rotation of the shaft 14 together with the guide wires 20 about the longitudinal axis L, the tool 16 can also be rotated permanently or endlessly relative to the control unit 18. By using the pivotable and rotatably mounted disc, the tool 16 can also be adjusted along the longitudinal axis L by the guide wires 20 at the same time for permanent rotation about the longitudinal axis L. As a result, the spatial orientation of the tool 16 can be compensated for permanent rotation of the shaft 14, the tool 16 rotating about its extension axis E with a rotational movement $\omega_E$. If the tool 16 is in a non-pivoted state, the extension axis E of the tool 16 corresponds to the longitudinal axis L of the shaft 14 and extends in the z-direction of the Cartesian coordinate system.

Since the guide wires 20 can rotate about the longitudinal axis L together with the shaft 14, an endless rotation about the longitudinal axis L or the extension axis E can be carried out by means of the drive 40 without twisting the guide wires 20 one into another to form a cord and without limiting or preventing control of the pivoting movement $\omega_x$, $\omega_y$.

Figure 2A:
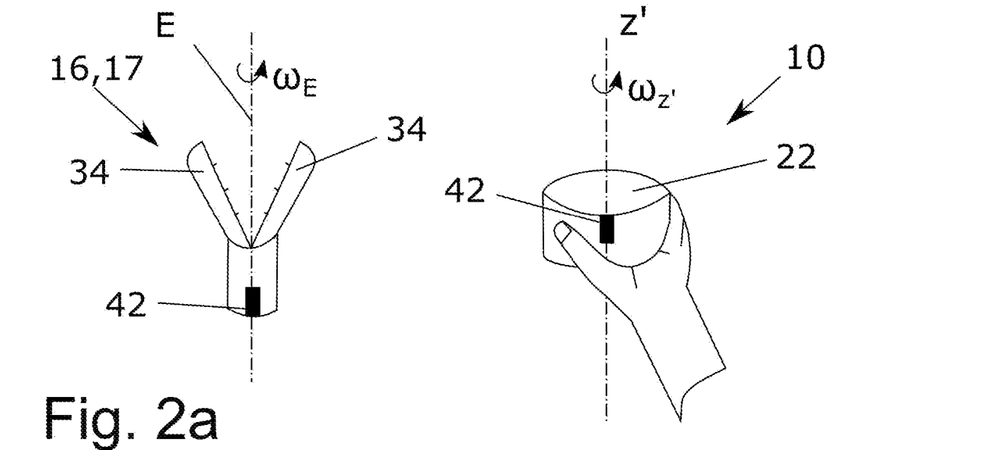
Figure 2B:
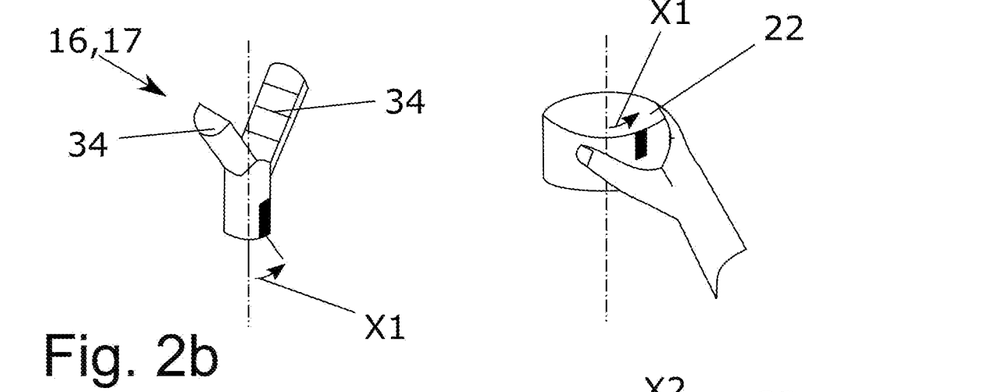
Figure 2C:
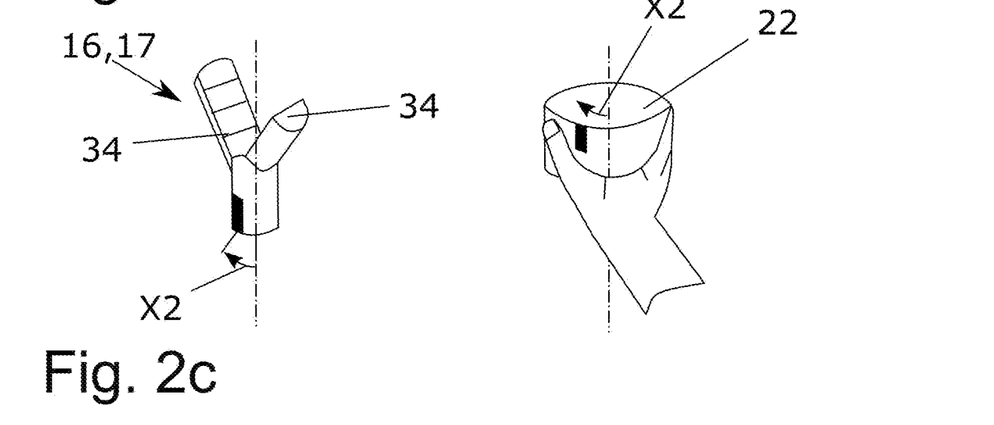

In FIGS. 2a to 2c, to illustrate the functioning of the first input means 22 of the input unit 10 according to an exemplary embodiment, the active principle when converting an ergonomic user input by an operator into handling of the tool 16 designed as a jaw part 17 is shown schematically.

In FIG. 2a, the input unit 10 and the jaw part 17 are shown in a rest position or a basic position, each with markings 42 to clarify the orientation.

In the present case, the first input means 22 are rotatable operating means and are shown as a tangible cylinder which is in operative contact by means of the control unit 18.

In an embodiment not shown, the operating means are designed as a control handle, in particular a joystick, which can be pivoted to a rest position and in particular a base plate, with a rotary element or rotary wheel, the rotary element being mounted so as to be rotatable about an extension axis of the control handle. User movements, in particular pivoting and/or rotational movements, can be detected by means of the control handle with rotary element in order to transmit these user movements to the tool 16 in the first handling mode in a true pivoting and/or rotational manner.

In a second embodiment, which is not illustrated, the operating means are in the form of a tweezer handle, preferably in the form of a cardan suspended pressure element. The tweezer handle has contact surfaces that can be gripped between the thumb and forefinger of one of the operator's hands, in particular, in order to deform the pressure element from a rest position by means of a force that can be applied by hand, in order to handle tool 16 and, for example, close a jaw part 17. Furthermore, the pressure element is coupled to a cardan suspension via a carrier element with a rotation mechanism in order to record all user movements acting on the pressure element, in particular pivoting and/or rotational movements, and to transfer them to the tool 16 in the first handling mode in a true pivoting and/or rotational manner.

For the sake of simplification, it is assumed that the ergonomic user input is only limited to a rotation of the jaw part 17 about its extension axis E in the first handling mode. The rotational movement $\omega_z$, of the first input means 22 and the rotational movement $\omega_E$ of the tool 16 are designed to be rotationally accurate to one another in the first handling mode, that is to say they have the same angular speeds in terms of amount.

In FIG. 2b, the first input means 22 were rotated anticlockwise by a first angular range X1, with this rotational movement being transmitted to the jaw part 17 at the correct angle. Furthermore, the first input means 22 were then rotated clockwise from the position illustrated in FIG. 2b by a second angular range X2 with reference to FIG. 2c, wherein here the jaw part 17 also follows the rotational movement of the first input means 22 in a rotation-true manner.

During ergonomic user input, the operator's hand always remains in contact with the first input means 22, so there should be no gripping around or brief interruptions in the first handling mode, since continuous and preferably uninterrupted imaging of the rotational movement $\omega_z'$ in the input means 22 are made in the rotational motion $\omega_E$ of the jaw part 17. An operator therefore has continuous and uninterrupted control over the adjustment movement of the tool 16, in particular in order to be able to carry out precise, complex, minimally invasive interventions and/or medical operations in a sensitive environment.

Due to the physiology of the human hand, the range of rotation is limited to a maximum angle of rotation of approximately ±90° about the resting position and thus a total of approximately 180° about the resting or basic position.

Figure 3A:
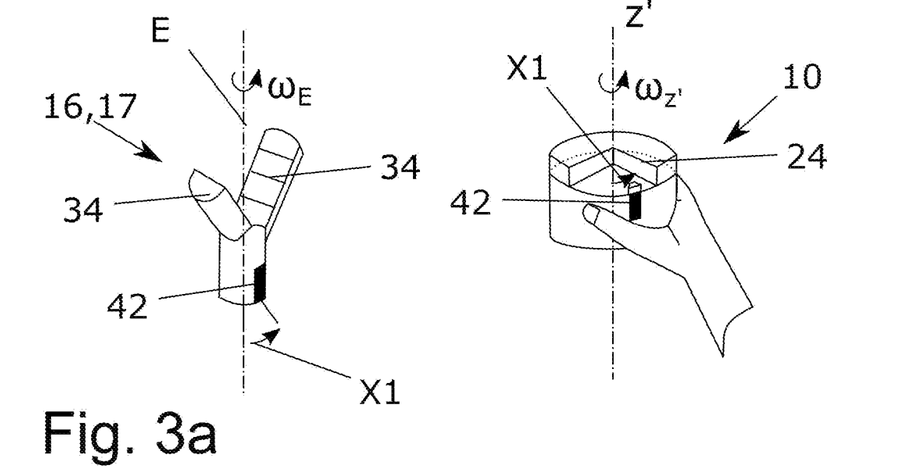
Figure 3B:
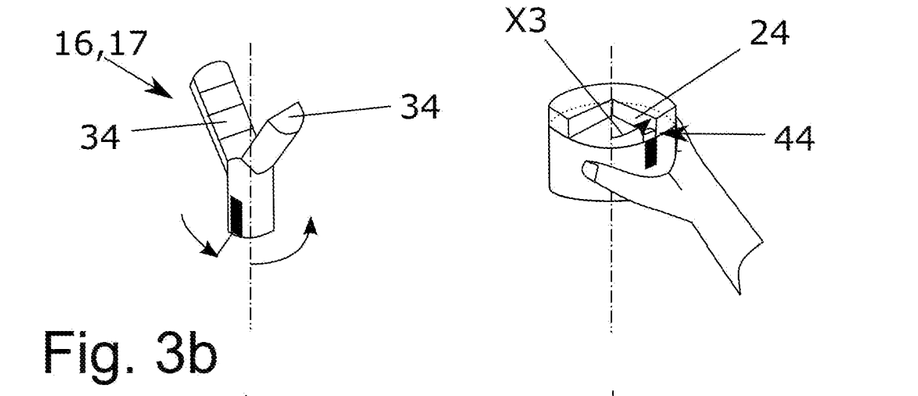
Figure 3C:
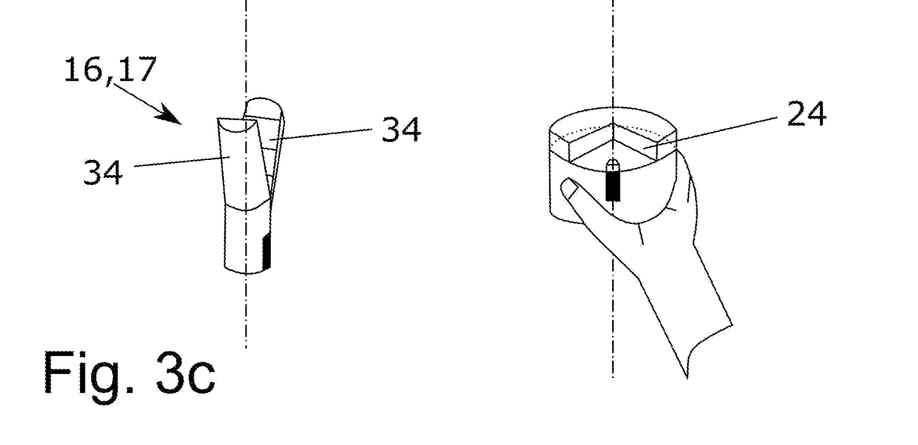

In FIG. 3a to FIG. 3c, in addition to the control of the tool 16 in the first handling mode, the tool 16 is also controlled via the second input means 24 in the second handling mode.

In the present case, the second input means 24 are formed by the identical tangible cylinder in order to control the tool 16 both in the first handling mode and in the second handling mode.

In FIG. 3a, as in FIG. 2b, the first input means 22 and therefore also the second input means 24 have been rotated anticlockwise from the basic position in FIG. 2a about the angular range X1, wherein the angular range X1 was reproduced in a rotation-true manner on the jaw part 17 and caused a corresponding rotation. The tool 18 was thus controlled in the first handling mode.

In FIG. 3b, the cylinder was rotated by a further user movement about the third angular range X3, which is larger than the first angular range X1, as a result of which the second input means 24 were guided to an end stop 44, in which an endless rotational movement of the jaw part 17 is activated. The jaw part 17 thus rotates endlessly about its extension axis E as a result of the further user input 21.

The second input means 24 are preferably embodied as switching means 500 (see FIGS. 4a to 5c) for switching the user input of the operating means between the first and the second handling mode, with the switching means 500 being activated by reaching and/or exceeding a threshold value of a force and/or the application of torque to the operating means can be switched over, and in this case it is particularly a matter of applying a torque to the rotatable operating means in opposition to the switching means 500 designed as a type of end stop or a mechanical pressure point.

In the above-described first embodiment of the operating means as a control handle with a rotary element, the switching means 500 preferably interact with the rotary element. In this case, the switching means 500 can be switched over by applying a torque or rotating movement to the rotary element in order to activate the second handling mode. Advantageously, the endless rotation of the tool can then also be controlled with the rotary element. Alternatively or additionally, the switching means 500 interact with the control handle, in particular in the base plate, in order to switch over the switching means 500 by applying a translatory force to the control handle along the extension axis.

In the second embodiment of the operating means described above, as a tweezers grip with rotatable pressure elements and a cardan suspension, the switching means 500 preferably interact with the rotatable pressure element, wherein the switching means 500 can also be switched to the second handling mode by applying a torque to the pressure element. Alternatively or additionally, the switching means 500 interact with the cardan suspension, wherein the switching means 500 can also be activated by applying a force and/or torque to the pressure element relative to the cardan suspension. As a further alternative or in addition, the switching means 500 can be activated by applying a force and/or torque to the pressure elements gripped like tweezers.

The endless rotation of the tool 16 is interrupted again by returning the second input means 24 to the basic position according to FIG. 3c. For this purpose, the second input means 24 are preferably mounted about the rest position against the first restoring means. The tool 16 does not, in particular not completely, follow the movement of the second input means 24 back into the basic position, so that the position of the markings 42 of the tool 16 and the input unit 10 can be adjusted relative to one another. It is thus advantageously enabled in the second handling mode by the second input means 24 that, in contrast to the operating principle of the first input means described with reference to FIGS. 2b and 2c, in the first handling mode, the speed of the rotational movement $\omega_E$ is not implemented in a rotation-true manner, at least in sections, in accordance with the further user input. However, further user input is still uninterrupted with the rotational movement $\omega_E$ of the tool 16 in order to ensure full control over the tool movement at all times. Advantageously, the ergonomically operable range of rotation is expanded as desired by the second input means 24 from approximately ±90° about the rest position or basic position, without the operator losing control of the jaw part 17 in the process.

In FIGS. 4a to 5b, the first input means 22 are shown schematically as an operating means 501 that can be moved translationally in a positioning direction 510 in a first adjusting section 504, wherein these movable operating means 501 are advantageously formed as the already described control handle with rotary element or rotatable tweezer handle with cardan suspension. The switching means 500 is shown schematically as the second input means 24 and is designed to switch the user input of the operating means 501 between the first and the second handling mode.

Figure 4A:
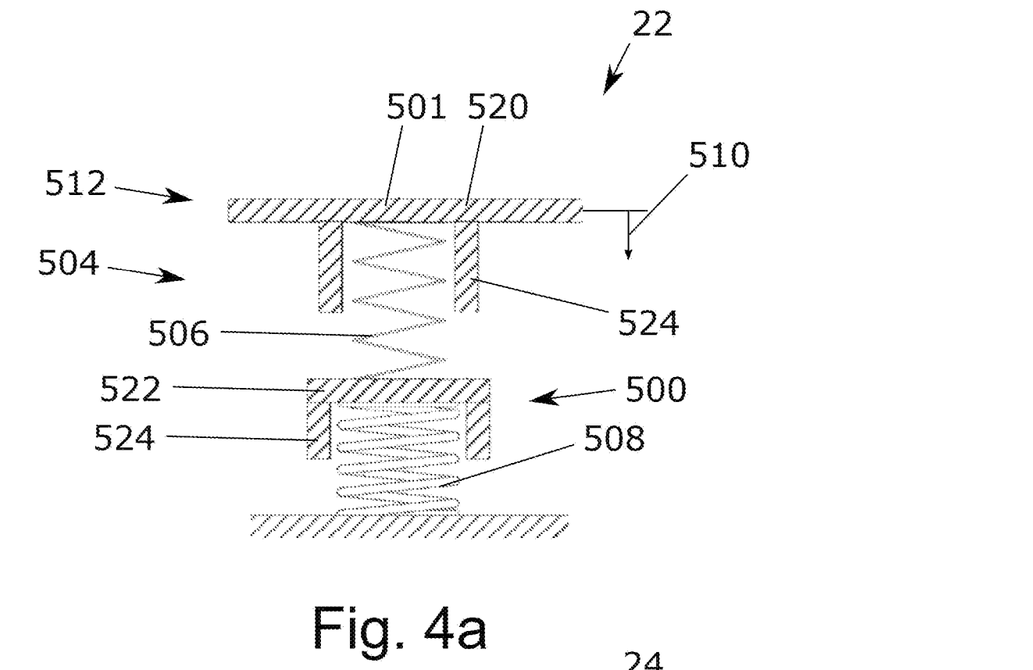
Figure 5A:
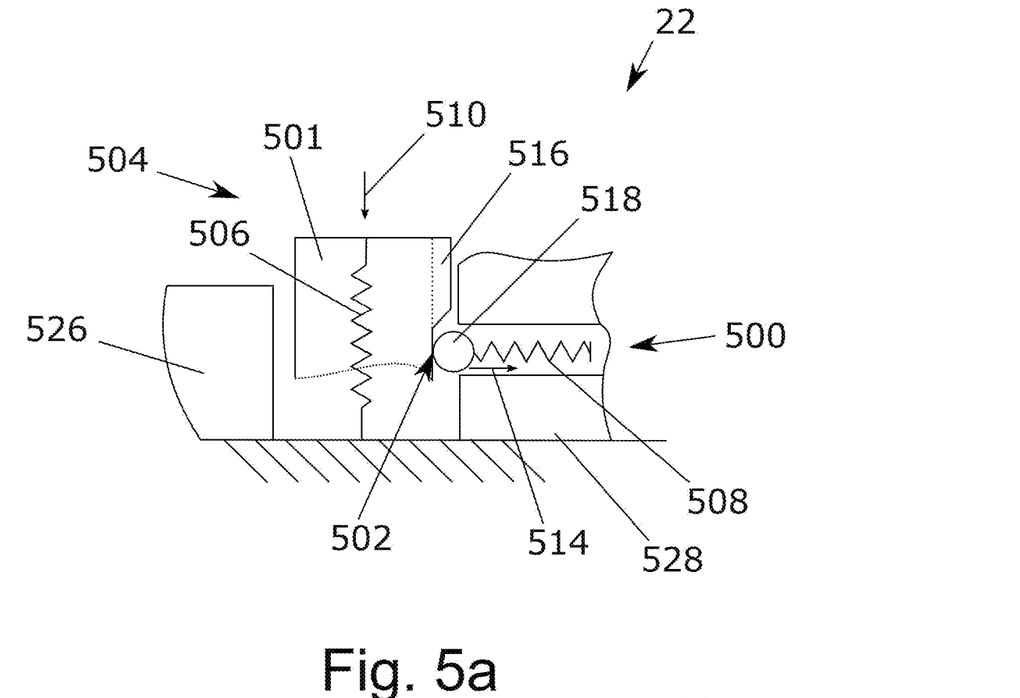
Figure 5B:
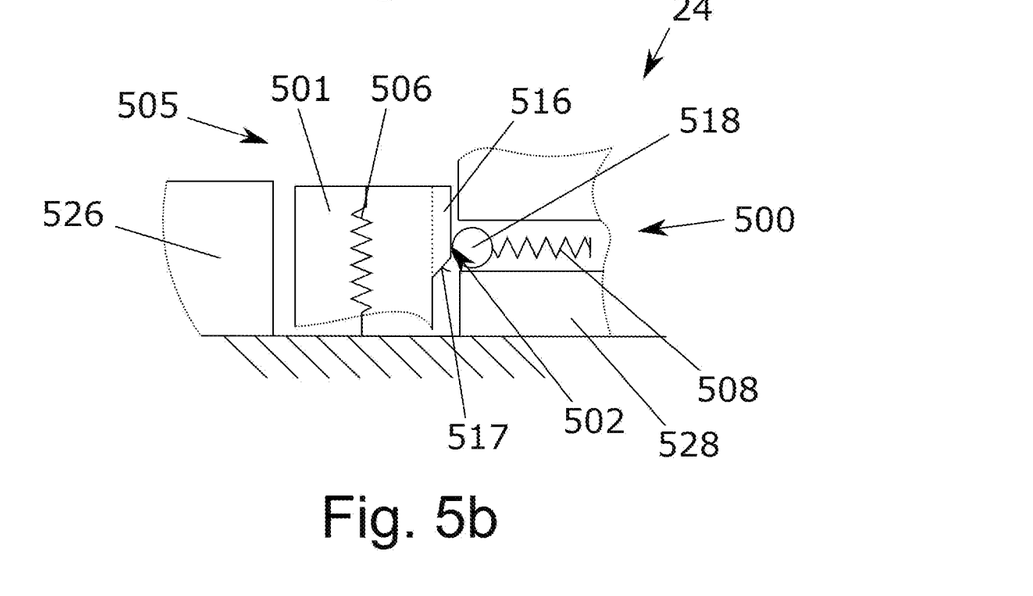

In FIG. 4a, the operating means 501 are mounted with the first resetting means 506 and the switching means 500 are mounted with the second resetting means 508.

The restoring means 506, 508 are designed as two pressure springs, with the first restoring means 506 having a lower spring stiffness than the second restoring means 508. The user input already described can be carried out by applying a force to the operating means 501 against the first restoring means 506.

The first restoring means 506 are mounted with a first guide sleeve 520 for receiving the user input. The second restoring means 508 are connected at one end to a second guide sleeve 522 in a series circuit with the first restoring means 506 and are fixedly mounted at the other end. The guide sleeves 520, 522 also have leg sections 524 to guide the restoring means 506, 508.

The series connection means that the two restoring means 506, 508 can be adjusted or deformed in the same adjusting direction 510, with the first guide sleeve 520 and the operating means 501 being shown here in a first adjusting section 504 for ergonomic user input in the first handling mode.

Figure 4B:
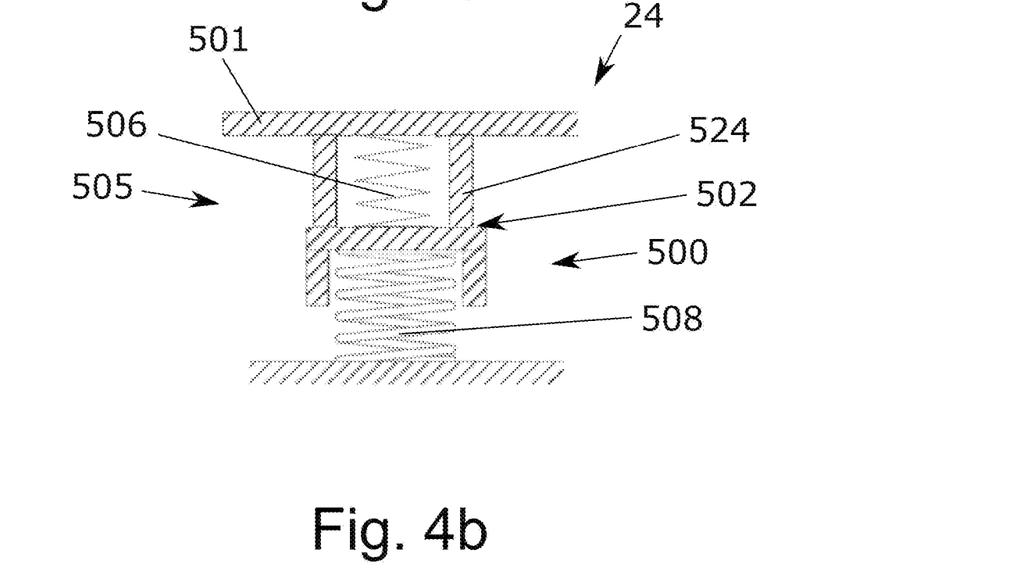

In FIG. 4b, the operating means 501 are adjusted in the adjusting direction 510 by applying a force and the first restoring means 506 are deformed, in particular as a compressed pressure spring. The leg sections 524 of the first guide sleeve 520 are in mechanical contact with the second guide sleeve 522 and thus form a mechanical stop 502. As a result of this mechanical stop 502, a threshold value for the application of force is at least reached and the second handling mode is activated by adjusting the switching means 500 and the second guide sleeve 522, and the operating means 501 control the further user input already described above against the second restoring means 508 and the endless rotational movement of the tool 16.

Due to the mechanical stop 502, only the second restoring means 508 counteract a user input in a second actuating section 505. Due to the increased spring stiffness of the second restoring means 508, the switching means 500 act as a type of pressure point or kick-down mechanism, with the resistance of the second restoring means 508 having to be reached or overcome by applying a force in the actuating direction 510 in order to trigger or activate the switching means 500 and the second handling mode.

Alternatively or in addition to the purely schematically illustrated embodiment, wherein an application of force in a translatory actuating direction 510 against a fixed clamping triggers or activates the switching means 500, the actuating direction 510 can be executed rotationally with rotatable operating means, in particular the rotatable tweezer handle or the rotary element of the control handle, and an application of torque, wherein the restoring means 506, 508 can then preferably also be executed as torsion springs and counteract the application of torque.

In general, first restoring means 506 therefore counteract the application of force and/or torque on the rotary element of the control handle or the rotatable tweezer handle in the first handling mode in order to transmit a pivoting and/or rotationally accurate movement to the tool 16. By deforming the first restoring means 506 and reaching and/or exceeding the threshold value of the application of force and/or torque, the operating means 501 activate the switching means 500 and the second handling mode. In this second handling mode, the operating means, in particular the control handle with rotary element and the rotatable tweezer handle, transmit a further user input, preferably a rotational movement counter to the second restoring means 508, into the endless rotational movement of the tool 16

FIG. 5a shows a further embodiment of the switching means 500, in which case the setting direction of the operating means 510 and the setting direction of the switching means 514 are arranged at an angle to one another and the first and second restoring means 506, 508 are mounted decoupled from one another. The operating means 501 and the switching means 500 are each mounted on a first and a second guide 526, 528 so that they can be displaced linearly or translationally. In particular, the first and second restoring means 506, 508 are shown as pressure springs, with the first and second restoring means 506, 508 being separately and firmly decoupled clamped at one end. Operating means 501 have a geometric projection 516, and switching means 500 comprise a ball 518, which can preferably be adjusted linearly in an actuating direction 514. In this case, the geometric projection 516 is designed in such a way that there is preferably no coupling or mechanical contact with the ball 518 in the illustrated first actuating section 504 for implementing the ergonomic user input in the first handling mode.

In FIG. 5b, as well as in FIG. 4b, the operating means 501 are adjusted linearly or translationally in the first guide 526 by the application of force, with the first restoring means 506 being shown as a pressure spring that is relatively compressed or deformed against fixed clamping and the geometric projection 516 together with the ball 518 form a mechanical stop 502. The geometric projection 516 has a chamfer at an angle to the actuating direction of the switching means 500 with a rolling or sliding surface 517 along which the ball 518 can roll or slide and thereby linearly or translationally counter the second restoring means 508 and is adjustable in the actuating direction of the switching means 514 with the second guide 528.

Here, the mechanical stop 502 of the ball 518 with the geometric projection 516 acts as a pressure point or as additional resistance to the user input, and a mechanically defined threshold value for the application of force to activate the switching means 500 can be set. The operating means 501 are therefore shown in the second actuating section 505, with the second handling mode being activated.

As an alternative or in addition to the translationally adjustable operating means 501 shown, the operating means 501 can also be rotatably mounted, in particular by means of a torsion spring as the first restoring means 506, in which case the geometric projection 516 is preferably arranged radially and by rotating the operating means 501 and applying a torque against preferably radially arranged ball 518, the switching means 500 are also switchable.

LIST OF REFERENCE NUMBERS

10 Input unit
12 Medical instrument
14 Shaft
16 Tool
17 Jaw part
18 Control unit
20 Guide wires
22 First input means
24 Second input means
30 Proximal end of the shaft
32 Distal end of the shaft
34 Jaw elements of the tool
36 Joint mechanism
38 Pivoting member
40 Drive
42 Marking
44 End stop
500 Switching means
501 Operating means
502 Mechanical stop
504 First actuating section
505 Second actuating section
506 First restoring means
508 Second restoring means
510 Actuating direction of the operating means
512 Series connection
514 Actuating direction of the switching means
516 Geometric projection
517 Chamfer with rolling or sliding surface
518 Bearing ball
520 First guide sleeve
522 Second guide sleeve
524 Leg sections
526 First lead
528 Second lead
1000 Medical system
E Tool extension axis
L Longitudinal axis of the shaft
R Axis of rotation
X1 First angular range
X2 Second angular range
X3 Third angular range
z' Extension axis of the input unit
x, y Spatial axes of the medical instrument
$\omega_E$ Rotational movement of the tool
$\omega_z'$ Rotational movement of the input unit
$\omega_x$, Pivoting movement of the tool
$\omega_y$ Pivoting movement of the tool

The invention claimed is:

1. An input unit configured to operate a medical instrument with a hollow shaft extending along a longitudinal axis and configured to receive guide wires, with a tool arranged distally on the shaft and a control unit arranged proximally on the shaft for handling the tool by means of the guide wires, comprising:
first input means for the continuous, pivoting and/or rotation-true, conversion of an ergonomically limited user input into an adjustment movement of the tool in a first handling mode in order to pivot the tool relative to the longitudinal axis by the control unit and/or to rotate it to a limited extent about the extension axis, wherein
the input unit has second input means for at least partially, non-absolutely converting at least one further user input into an endless rotational movement ($\omega_E$) of the tool about its extension axis in a second handling mode, wherein the first input means are configured as operating means that can be moved in a first actuating section and the second input means are configured as switching means for switching the user input of the operating means limited by the switching means between the first and the second handling mode, wherein the switching means can be switched by reaching and/or exceeding a force and/or torque on the operating means.

2. The input unit according to claim 1, wherein that the switching means with the operating means in a second actuating section of the operating means form a mechanical stop, in particular a pressure point, for switching between the first and the second handling mode.

3. The input unit according to claim 2, wherein that the operating means comprise first restoring means and the switching means comprise second restoring means, with a restoring force and/or torque of the second restoring means forming the threshold value for switching over the switching means.

4. The input unit according to claim 3, wherein the first and the second restoring means are coupled in a series connection, the first restoring means connecting the operating means with the switching means and wherein the first restoring means are adjustable or deformable in such a way that when the threshold value of the application of force and/or torque is reached and/or exceeded, the mechanical stop is formed.

5. The input unit according to claim 4, wherein a restoring force and/or torque of the first restoring means, which can be adjusted in particular by spring stiffness, is smaller than that of the second restoring means.

6. The input unit according to claim 4, wherein the first and the second restoring means are coupled in the series connection and act in a same adjusting direction.

7. The input unit according to claim 3, wherein
the first and second restoring means are decoupled and the setting direction of the operating means and the setting direction of the switching means are arranged relative to one another and the mechanical stop upon reaching and/or exceeding the threshold value is formed by a geometric projection in the operating means.

8. The input unit according to claim 7, wherein
the switching means are configured as a linearly adjustable ball in order to roll or slide in mechanical contact with the operating means on their geometric projection, in particular a chamfer with a rolling or sliding surface.

9. The input unit according to claim 7, wherein
the operating means are rotatably mounted, by of a torsion spring as the first restoring means, the geometric projection being arranged radially.

10. The input unit according to claim 3, wherein
the first and/or the second restoring means are designed as a pressure spring and/or a torsion spring.

11. The input unit according to claim 1, wherein
the operating means are designed as a pivotable and/or rotatable joystick with a rotary element or a rotatable tweezer grip with a cardan suspension.

12. A medical system with at least one input unit according to claim 1, and with at least one medical instrument, comprising a hollow shaft extending along the longitudinal axis configured for receiving guide wires for a tool, the tool arranged on the distal side of the shaft and formed along an extension axis for medical use on patients, a control unit arranged proximally on the shaft and operatively connected to the tool via the guide wires to move the tool in a first handling mode and in a second handling mode.

13. The medical system according to claim 12, wherein
the medical system comprises a spatially adjustable disc which is in operative contact with the guide wires to pivot the tool along the longitudinal axis of the shaft by means of the guide wires, wherein the disc together with the shaft and the guide wires is endlessly rotatable about the longitudinal axis.

14. The medical system according to claim 13, wherein the pivoting of the tool along the longitudinal axis is limited.

15. The medical system of claim 12, wherein the medical system is one or more of an end effector and a surgical robot.

16. The input unit according to claim 1, wherein first input means for the continuous, pivoting and/or rotation-true conversion of an ergonomically limited user input is uninterrupted and/or absolute.

17. The medical system according to claim 1, wherein the first input means is a tangible cylinder.

18. The medical system according to claim 1, wherein the second input means is a tangible cylinder.

19. The medical system according to claim 1, wherein the switching means is a mechanical stop or pressure point.

* * * * *